(12) United States Patent
Merkley et al.

(10) Patent No.: US 10,434,002 B2
(45) Date of Patent: Oct. 8, 2019

(54) ORTHOTIC STRAPPING SYSTEM

(71) Applicants: Lorin Merkley, Gilbert, AZ (US); Jared Howell, Manvel, TX (US)

(72) Inventors: Lorin Merkley, Gilbert, AZ (US); Jared Howell, Manvel, TX (US)

( * ) Notice: Subject to any disclaimer, the term of this patent is extended or adjusted under 35 U.S.C. 154(b) by 0 days.

(21) Appl. No.: 14/584,000

(22) Filed: Dec. 29, 2014

(65) Prior Publication Data

US 2015/0119778 A1 Apr. 30, 2015

Related U.S. Application Data

(63) Continuation of application No. 13/589,299, filed on Aug. 20, 2012, now Pat. No. 8,920,350.

(60) Provisional application No. 61/525,189, filed on Aug. 19, 2011.

(51) Int. Cl.
*A61F 5/01* (2006.01)

(52) U.S. Cl.
CPC .............. *A61F 5/0123* (2013.01); *A61F 5/01* (2013.01); *A61F 5/0102* (2013.01); *A61F 2005/0137* (2013.01)

(58) Field of Classification Search
CPC .... A61F 5/0102; A61F 5/0123; A61F 5/0125; A61F 5/0106; A61F 5/01; A61F 2005/0137

USPC ................................................ 602/16, 23–28
See application file for complete search history.

(56) References Cited

U.S. PATENT DOCUMENTS

| | | | | |
|---|---|---|---|---|
| 4,361,142 A | * | 11/1982 | Lewis | A61F 5/0123 602/16 |
| 4,856,500 A | | 8/1989 | Spademan | |
| 5,002,045 A | | 5/1991 | Spademan | |
| 5,599,288 A | | 2/1997 | Shirley | |
| 6,551,264 B1 | * | 4/2003 | Cawley | A61F 5/0125 128/882 |
| 7,435,234 B2 | * | 10/2008 | Gamada | A61F 5/0123 602/16 |
| 8,920,350 B2 | * | 12/2014 | Merkley | A61F 5/0102 602/16 |
| 2005/0245853 A1 | * | 11/2005 | Scorvo | A61F 5/0125 602/16 |
| 2005/0273025 A1 | * | 12/2005 | Houser | A61F 5/0123 602/16 |

* cited by examiner

*Primary Examiner* — Tarla Patel
(74) *Attorney, Agent, or Firm* — Useful Arts IP

(57) ABSTRACT

An orthotic strapping system that loosens all or a portion of a strap by capturing the angular movement of an orthotic joint to move the attachment point of the strap. This can be done with cabling or by using rotating cams and rigid linkages to connect them.

10 Claims, 7 Drawing Sheets

ORTHOTIC STRAPPING SYSTEM

BACKGROUND OF THE INVENTION

The present invention is in the technical field of orthotic devices. More particularly, the present invention is in the technical field of orthotic strapping.

Orthotic devices are generally attached and suspended on the body using a strapping system. This strapping system allows the orthosis to aid or replace musculoskeletal movement and function. Conventional strapping systems are static and unchanging once they are applied and tightened. When applying an orthosis with static straps, there is very often migration or discomfort when applied to a dynamic joint of the body. For example a strap behind the popliteal portion of the leg often impinges on the hamstring tendons as the knee joint flexes from an extended position, causing pain. The static strapping also leads to migration since the anatomy around the joint is moving, but the brace and straps are not.

DETAILED DESCRIPTION

Summary

A dynamic strapping system for an orthosis is described that changes with the changing anatomy of a braced joint.

Description

Figure 1:
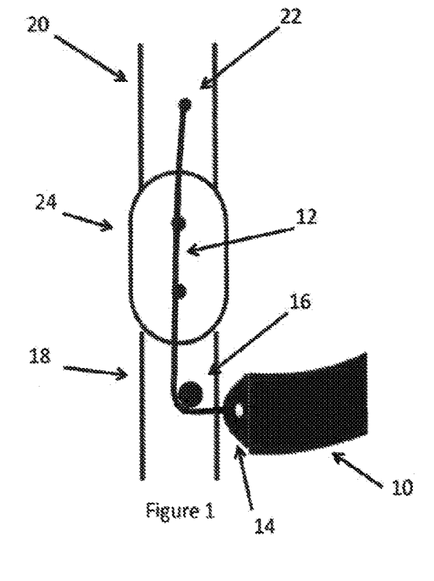
FIG. 1 is a perspective view of a dynamic strapping system.
Figure 2:
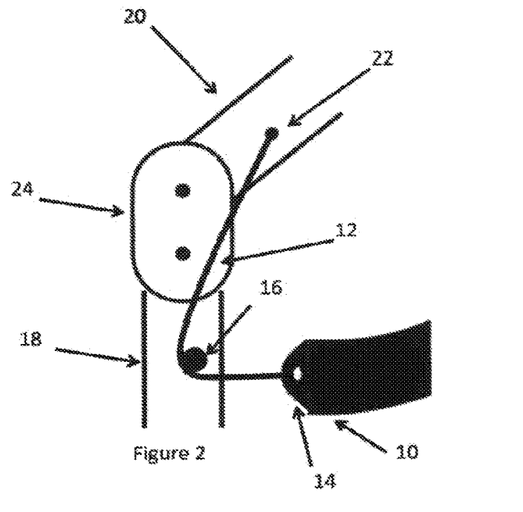
FIG. 2 is a side view of a dynamic strapping system of FIG. 1 through an angular change.

Referring now to the present dynamic strapping system in more detail, in FIG. 1 and FIG. 2 there is shown a strap 10 attached to dynamic driving mechanism 12 by means of a strap attachment 14. The driving mechanism 12 is directed by a direction changing mechanism 16 which is attached to the distal orthotic frame segment 18. The driving mechanism for the strapping system is connected proximally to the proximal orthotic frame segment 20 by the driving mechanism attachment 22. There is a polycentric joint 24 connecting the proximal orthotic frame segment 20 and the distal orthotic frame segment 18.

In more detail, still referring to the dynamic strapping system of FIG. 1 and FIG. 2 the strap 10 is able to tighten and loosen by a change in the tension or placement of the driving mechanism 12. The direction and magnitude of this change is controlled by the direction changing mechanism 16 and is powered by the angular change of the proximal orthotic frame 20 relative to the distal orthotic frame 18 as they change with the changing physiology of the joint through human locomotion.

In further detail, still referring to the dynamic strapping system of FIG. 1 and FIG. 2 the driving mechanism attachment 22 may be attached to the frame in such a position as to allow for the strap 10 to not loosen until a significant angular change, for example in the range 15-40 degrees, has occurred. This attachment point could be but is not limited to 1" proximal to the joint and at the midline of the proximal orthotic frame 18. The driving mechanism 12 is sufficiently long enough to travel from the driving mechanism attachment 22 to the strap attachment. The direction changing mechanism is attached on the distal orthotic frame 18 so as to put the strap 10 in a position that is proximal to the gastroc muscle belly of the wearer and in the popliteal fossa. The strap may be a standard length for a knee brace, for example.

The construction details of the dynamic strapping system as shown in FIG. 1 and FIG. 2 may vary. The proximal orthotic frame 20 and the distal orthotic frame 18 can be made of a rigid or semi-compliant material such as metals, composites, or polymers. The driving mechanism 12 can be constructed of any flexible yet strong material such as cable, perlon, spectralon, and the like. The strap 10 can be made of any flexible webbing material. The direction changing mechanism 16 can be constructed of any material hard enough and durable enough to support the forces created and to resist wear such as dense polymers, metals, or the like.

Figure 3:
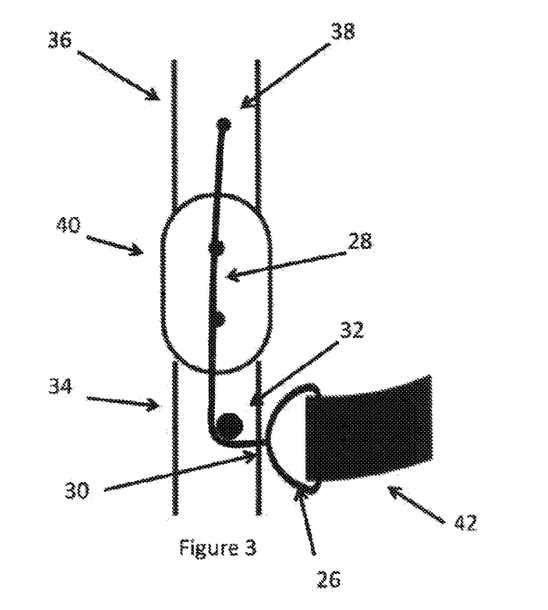
FIG. 3 is a side view of a dynamic strapping system.
Figure 4:
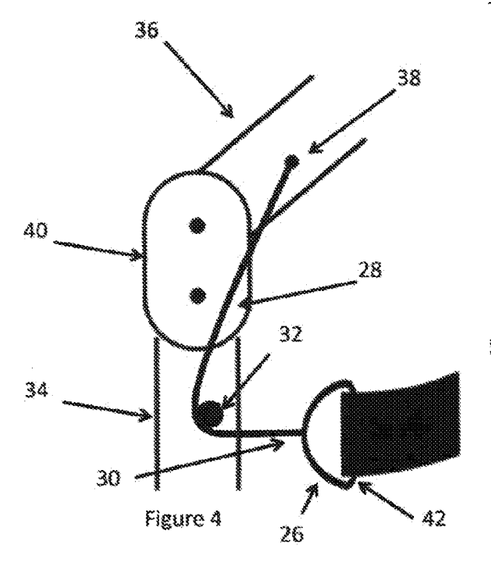
FIG. 4 is a side view of a dynamic strapping system of FIG. 3 through an angular change.

Referring now to the dynamic strapping system in more detail, in FIG. 3 and FIG. 4 there is shown a strap chafe 26 attached to dynamic driving mechanism 28 by means of a strap attachment 30. The strap chafe has a strap 42 through it that wraps around the wearers leg. The driving mechanism 28 is directed by a direction changing mechanism 32 which is attached to the distal orthotic frame segment 34. The driving mechanism for the strapping system is connected proximally to the proximal orthotic frame segment 36 by the driving mechanism attachment 38. There is a polycentric joint 40 connecting the proximal orthotic frame segment 36 and the distal orthotic frame segment 34.

In more detail, still referring to the dynamic strapping system of FIG. 3 and FIG. 4 the strap 42 is able to tighten and loosen by the movement of the chafe 26 which is made by a change in the tension or placement of the driving mechanism 28. The direction and magnitude of this change is controlled by the direction changing mechanism 32 and is powered by the angular change of the proximal orthotic frame 36 relative to the distal orthotic frame 34 as they change with the changing physiology of the joint through human locomotion.

In further detail, still referring to the dynamic strapping system of FIG. 3 and FIG. 4 the driving mechanism attachment 38 may be attached to the frame in such a position as to allow for the strap 42 to not loosen until a significant angular change, for example in the range 15-40 degrees, has occurred. This attachment point could be but is not limited to 1" proximal to the joint and at the midline of the proximal orthotic frame 36. The driving mechanism 28 is sufficiently long enough to travel from the driving mechanism attachment 38 to the strap attachment. The direction changing mechanism 32 is attached on the distal orthotic frame 34 so as to put the strap 10 in a position that is proximal to the gastroc muscle belly of the wearer and in the popliteal fossa. The strap may be a standard length for a knee brace, for example.

The construction details of the dynamic strapping system as shown in FIG. 3 and FIG. 4 may vary. The proximal orthotic frame 36 and the distal orthotic frame 34 can be made of a rigid or semi-compliant material such as metals, composites, or polymers. The driving mechanism 28 can be constructed of any flexible yet strong material such as cable, perlon, spectralon, and the like. The strap 42 can be made of any flexible webbing material. The direction changing mechanism 32 can be constructed of any material hard enough and durable enough to support the forces created and to resist wear such as dense polymers, metals, or the like. The chafe 26 can be constructed of any hard durable material such as metal or a hard plastic.

Figure 5:
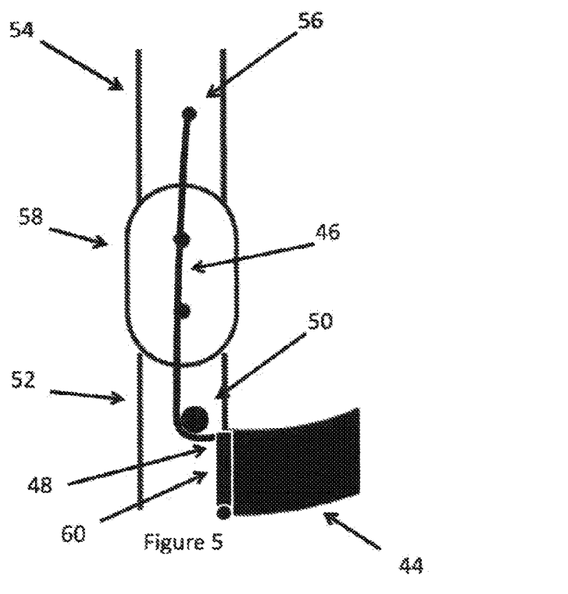
FIG. 5 is a side view of a dynamic strapping system.
Figure 6:
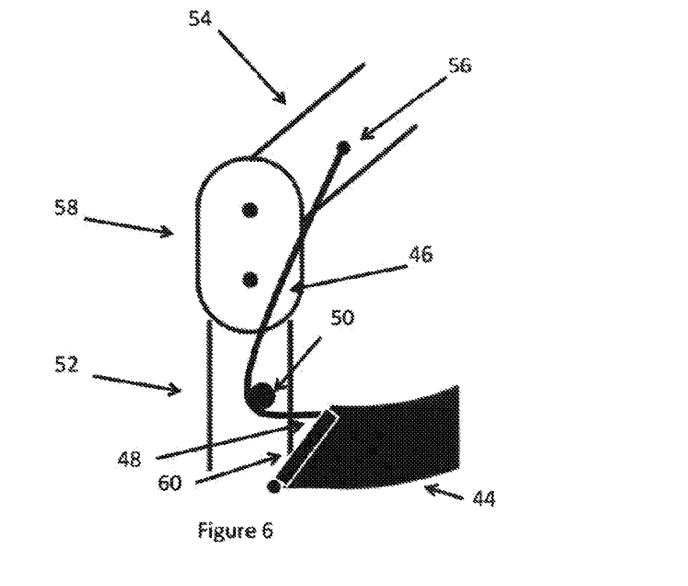
FIG. 6 is a side view of a dynamic strapping system of FIG. 5 through an angular change.

Referring now to the dynamic strapping system in more detail, in FIG. 5 and FIG. 6 there is shown a strap 44 attached to dynamic driving mechanism 46 by means of a strap attachment 48 on the superior border of the strap 44. The inferior border of the strap end is attached to the distal orthotic frame segment 52. There is a rigid member 60 connecting the superior and inferior borders of the strap 44 end. The driving mechanism 46 is directed by a direction changing mechanism 50 which is attached to the distal orthotic frame segment 52. The driving mechanism 46 for the strapping system is connected proximally to the proximal orthotic frame segment 54 by the driving mechanism attachment 56. There is a polycentric joint 58 connecting the proximal orthotic frame segment 54 and the distal orthotic frame segment 52.

In more detail, still referring to the dynamic strapping system of FIG. 5 and FIG. 6 the superior border of the strap 44 is able to tighten and loosen by a change in the tension or placement of the driving mechanism 12. The rigid member 60 allows the strap 44 to remain static on the inferior border of the strap 44 but to change only on the superior border. The direction and magnitude of this change is controlled by the direction changing mechanism 50 and is powered by the angular change of the proximal orthotic frame 54 relative to the distal orthotic frame 52 as they change with the changing physiology of the joint through human locomotion.

In further detail, still referring to the dynamic strapping system of FIG. 5 and FIG. 6 the driving mechanism attachment 56 may be attached to the frame in such a position as to allow for the strap 44 to not loosen until a significant angular change, for example in the range 15-40 degrees, has occurred. This attachment point could be but is not limited to 1" proximal to the joint and at the midline of the proximal orthotic frame 54. The driving mechanism 46 is sufficiently long enough to travel from the driving mechanism attachment 56 to the strap attachment 48. The direction changing mechanism is attached on the distal orthotic frame 52 so as to put the strap 44 in a position that is proximal to the gastroc muscle belly of the wearer and in the popliteal fossa. The strap may be as standard length for a knee brace, for example.

The construction details of the dynamic strapping system as shown in FIG. 5 and FIG. 6 may vary. The proximal orthotic frame 54 and the distal orthotic frame 52 can be made of an rigid or semi compliant material such as metals, composites, or polymers. The driving mechanism 46 can be constructed of any flexible yet strong material such as cable, perlon, spectralon, and the like. The strap 44 can be made of any flexible and elastic webbing material. The rigid member 60 can be constructed of any rigid material. The direction changing mechanism 50 can be constructed of any material hard enough and durable enough to support the forces created and to resist wear such as dense polymers, metals, or the like.

Figure 7:
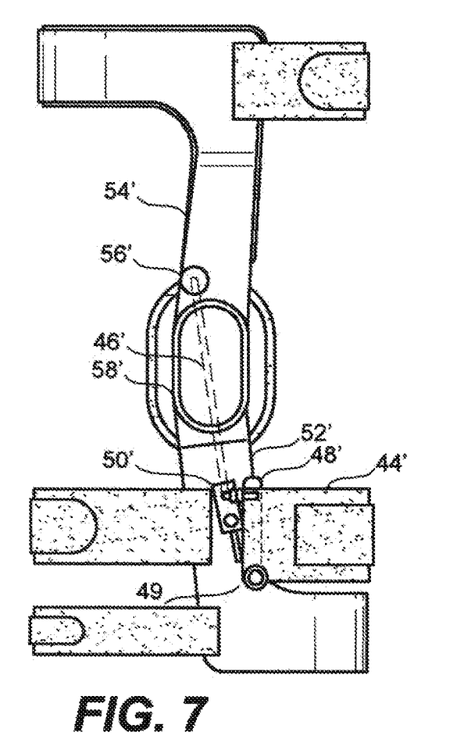
FIG. 7 is a diagram of a knee brace constructed in accordance with the principles of FIGS. 5 and 6.

Referring to FIG. 7, a diagram is shown of one example of a knee brace constructed in accordance with the principles of FIGS. 5 and 6. Orthotic frames 54' and 52' (thigh and shin) are joined by a polycentric joint 58'. A line 46' such as a cable or cord forms a driving mechanism. In this embodiment, the line 46' runs on the inside of the knee brace and is largely hidden from view. The line 46' attaches to the orthotic frame 54' at an attachment point 56', which may take the form of a hole and, optionally, a bushing. A direction changing mechanism 50' changes the direction of motion of the line prior to it attaching to a strap 44' by means of a rigid member 48', such as a bar or the like. The direction changing mechanism 50' may take the form of a hole and, optionally, a bushing. The rigid member 48' is attached to the knee brace at a pivot point 49.

Figure 8:
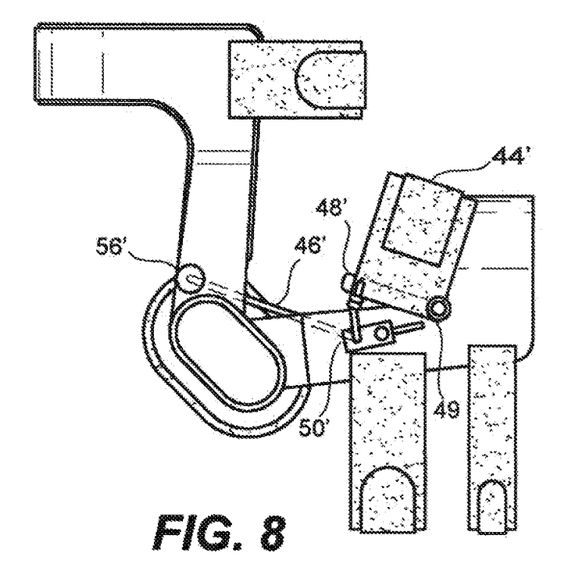
FIG. 8 is another view of the knee brace of FIG. 7.

Referring to FIG. 8, the knee brace of FIG. 7 is shown in a bent position, such as a kneeling position. In order to provide the most comfort when sitting, kneeling, crouching, etc., it is desirable for the strap to be loosened somewhat. This is accomplished in the embodiment of FIG. 8 as the attachment point 56' and the direction changing mechanism are brought closer together as a result of the bent position of the knee brace. The tension of the strap 44' causes the line 46' to be drawn through the direction changing mechanise 50'. As the rigid member 48' pivots about the pivot point 49, the tension the strap 44' is relaxed.

Figure 9:
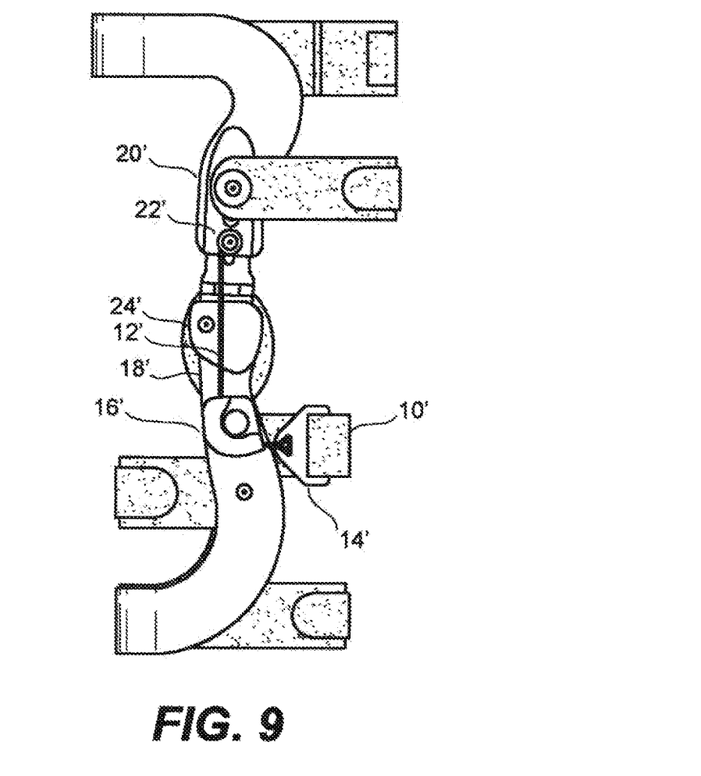
FIG. 9 is a diagram of a knee brace constructed in accordance with the principles of FIGS. 1 and 2.

Referring to FIG. 9, a diagram is shown of one example of a knee brace constructed in accordance with the principles of FIGS. 1 and 2. Orthotic frames 20' and 18' (thigh and shin) are joined by a polycentric joint 24'. A line 12' such as a cable or cord forms a driving mechanism. The line 12' attaches to the orthotic frame 20' at an attachment point 22'. A direction changing mechanism 16' changes the direction of motion of the line prior to it attaching to a strap 10' by means of a strap attachment 14'.

The direction changing mechanism 16' may take any of various forms. In the illustrated embodiment, the direction changing mechanism is a thermoformed plastic member having embedded therein a conduit through which the line 12' is passed. In other embodiments, the direction changing member may be a simple pulley, a pulley provided with a retaining member, etc. Another direction changing member may take the form of a post formed of two threaded halves each having a channel formed therein. When the halves are threaded together, the channels mate to form a conduit. In another embodiment, a circular groove is formed in a pin to accommodate the line. An annulus fits over the pin. The annulus is slotted perpendicular to the axis thereof, the slot extending through an angle slightly greater than ninety degrees. The slot allows the line to enter and exit the combined structure. Various other constructions will be apparent to those skilled in the art.

Figure 10:
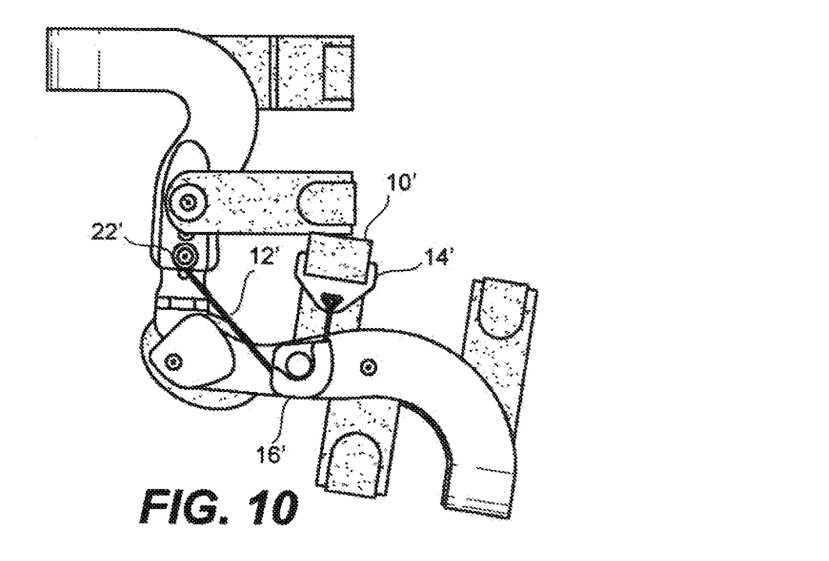
FIG. 10 is another view of the knee brace of FIG. 9.

Referring to FIG. 10, the knee brace of FIG. 9 is shown in a bent position, such as a kneeling position. In order to provides the most comfort when sitting, kneeling, crouching, etc., it is desirable for the strap to be loosened somewhat. This is accomplished in the embodiment of FIG. 10 as the attachment point 20' and the direction changing mechanism 16' are brought closer together as a result of the bent position of the knee brace. The tension of the strap 10' causes the line 12' to be drawn through the direction changing mechanism 16'. As a result, the tension of the strap 10' is relaxed.

Various other embodiments are illustrated in FIGS. 11-16.

Figure 13:
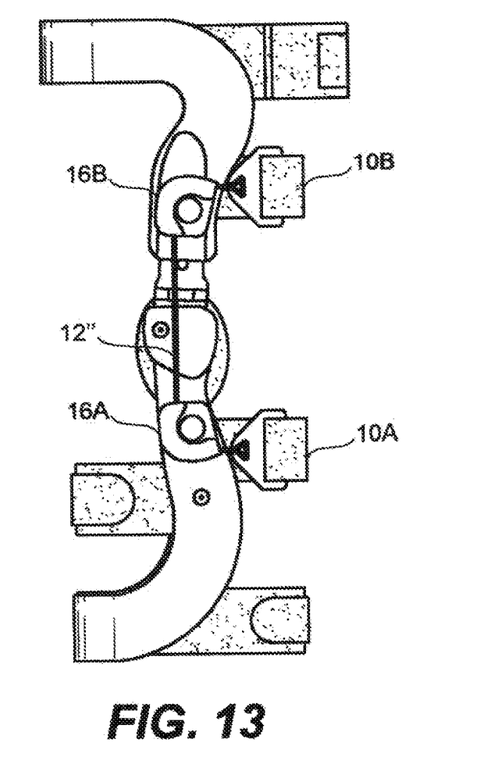
FIG. 13 is a diagram of a further dynamic strapping system.
Figure 14:
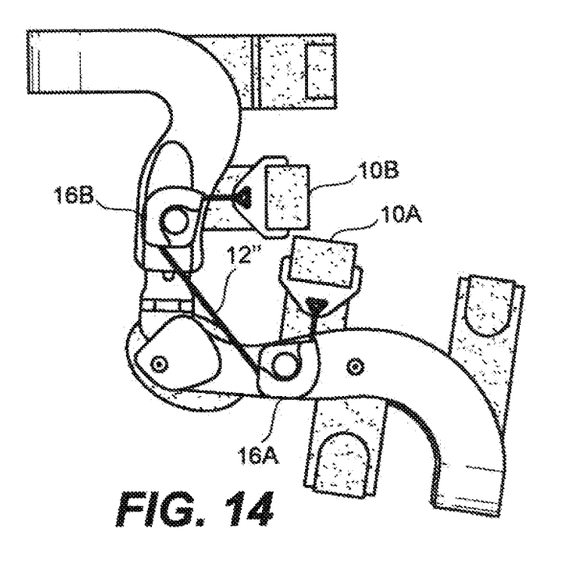
FIG. 14 is another view of the dynamic strapping system of FIG. 13.

Referring to FIG. 13, in this embodiment, two coordinated strap tensioning mechanisms are provided to vary the tension of two different straps. A direction changing mechanism, or redirector 16A is coupled to a strap 10A. Another redirector 16B is coupled to a strap 10B. A line 12" runs through both of the redirectors 16A and 16B and is coupled to both of the straps 10A and 10B. As flexion of the joint increases (FIG. 14), the line 12" relaxes, allowing both the straps 10A and 10B to loosen.

Figure 11:
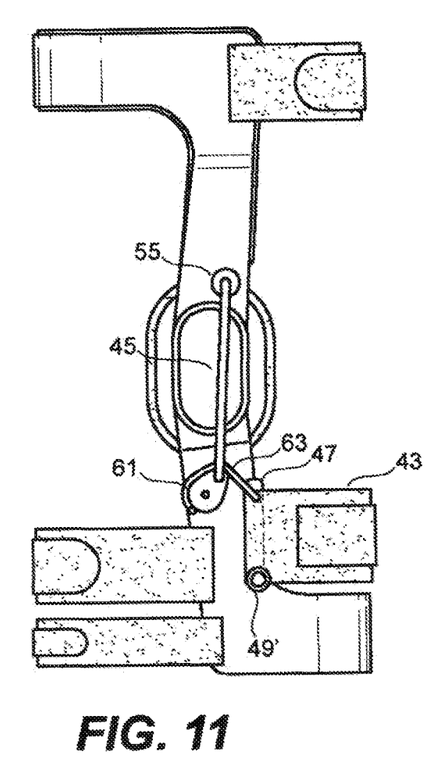
FIG. 11 is a diagram of another knee brace constructed in accordance with the principles of FIGS. 1 and 2.
Figure 12:
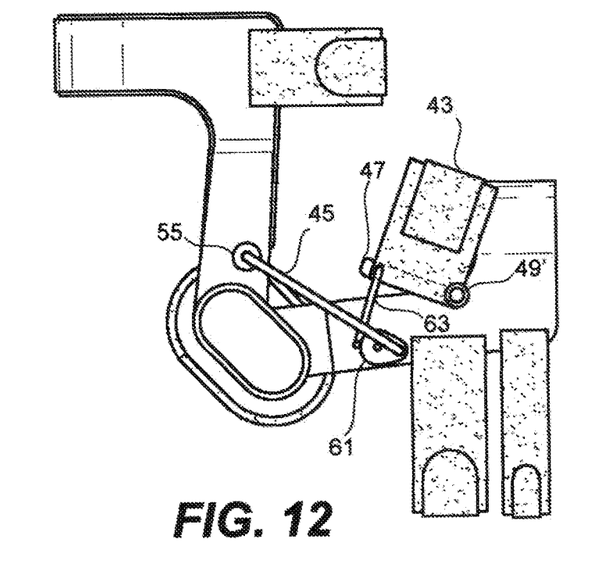
FIG. 12 is another view of the knee brace of FIG. 11.

A more rugged construction of an orthotic strapping system is shown in FIGS. 11 and 12. In this embodiment, instead of a line, a solid linkage such as a rod 45 is used. The rod attaches to the orthosis at an attachment point 55 and operates a cam 61, which rotates to tighten and loosen a strap 43. As in previous embodiments, the strap 43 may be attached by means of a rigid member 47 and a pivot point 49'. A flexible linkage 63 (e.g., line, cable, etc.) attaches to the rigid member 47 and to the cam 61, and follows the contour of the cam 61 along a length thereof. As flexion of the joint increases, the rod 45 causes the earn 61 to rotate, causing the flexible linkage 63 to unwind from the cam 61 and causing the strap 43 to loosen.

Figure 15:
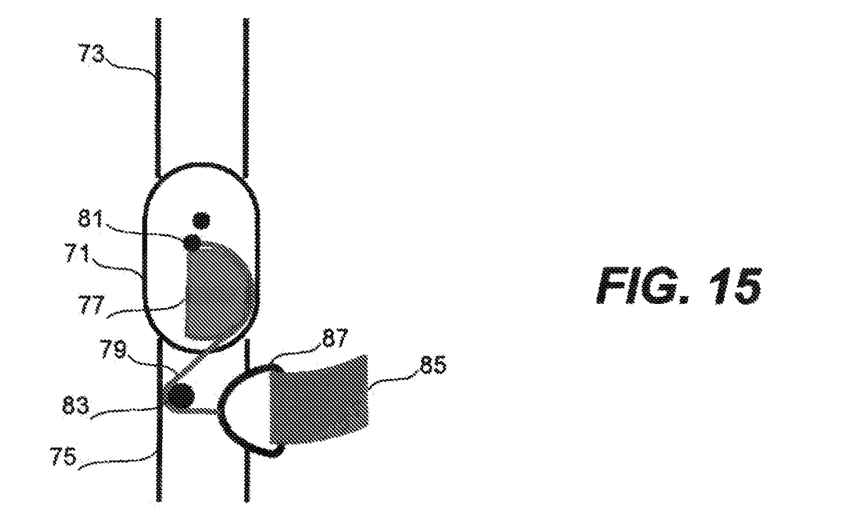
FIG. 15 is a diagram of still another dynamic strapping system.
Figure 16:
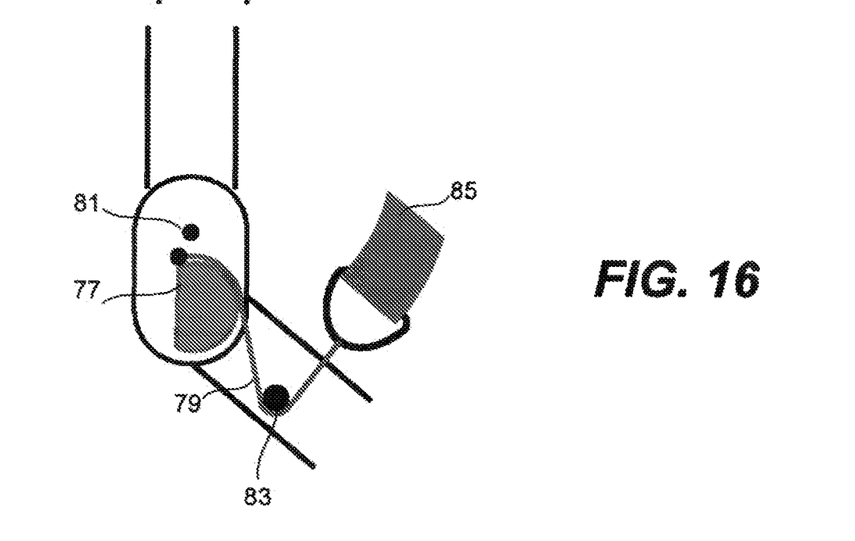
FIG. 16 is another view of the dynamic strapping system of FIG. 15.

Referring to FIGS. 15 and 16, in this embodiment, a strap tensioning mechanism is provided as part of the polycentric joint. More particularly, a polycentric joint 71 joins first and second orthotic support members 73 and 75. Within the joint 71 is provided a contoured member 77. A line 79 is attached at an attachment point 81, wraps around the contoured member 77 and exits the bottom of the joint 71. A direction changing mechanism 83 changes the direction of motion of the line 79, which then attaches to a strap 85, via a chafe 87 for example. As shown in FIG. 16, with increasing flexion of the joint, the line 79 unwraps from the contoured member 77 and lengthens, loosening the strap.

The advantages of the present dynamic strapping system include, without limitation, additional comfort in the popliteal region to the wearer of the orthotic device due to the adapting of the brace to the changing physiology of the wearer. The present dynamic strapping system also has the ability to aid in promoting suspension of the orthotic device on the wearer's anatomy In broad embodiment, the present invention is a strapping system that varies tension of (e.g., loosens) all or a portion of the strap. This may be done by capturing the angular movement of the joint to move the attachment point of the strap. Such movement may be done with cabling or by using rotating cams and rigid linkages to connect them, or by a combination of any of the aforementioned methods, and is not limited only to the figures and description listed above.

While the foregoing written description of the invention enables one of ordinary skill to make and use what is considered presently to be the best mode thereof those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

What is claimed is:

1. A strapped brace for supporting a joint of a wearer, comprising a strap and a strap tensioning mechanism, configured to vary tension of the strap with increasing flexion of the joint and vary tension of the strap with decreasing flexion of the joint further comprising a first member and a second member coupled in hinged relation to one another, wherein the strap is coupled to at least one of the first member and second member for securing the strapped brace to the wearer; wherein the strap tensioning mechanism comprises a line coupled to the strap and to at least one of the first member and the second member and is configured such that tension of the strap is varied in accordance with relative positions of the first member and the second member; wherein the strap tensioning mechanism comprises a direction changing mechanism comprising an enclosed arcuate channel through which the line passes for translating motion of the line from one direction to another different direction in response to movement of the at least one of the first member and second member.

2. The apparatus of claim 1, wherein the line is directly attached to the strap.

3. The apparatus of claim 1, wherein the line is coupled to the strap via a chafe.

4. The apparatus of claim 1, wherein the line is at least partially hidden.

5. The apparatus of claim 1, wherein the strap comprises a rigid member extending in
   a direction from one edge of the strap to another edge of the strap.

6. The apparatus of claim 5, wherein the rigid structure is coupled to one of the first
   member and the second member so as to allow for a pivoting motion about one end of the rigid member.

7. The apparatus of claim 6, wherein the line is coupled to an end of the rigid member opposite the one end.

8. The apparatus of claim 1, wherein the strapped brace is a knee brace.

9. The apparatus of claim 8, wherein, when the strapped brace is worn, the strap
   adjoins a popliteal fossa of the user.

10. The apparatus of claim 1, comprising a second strap and a second strap tensioning mechanism, configured to vary tension of the second strap with increasing flexion of the joint and vary tension of the strap with decreasing flexion of the joint.

* * * * *